United States Patent

Kumar

Patent Number: 5,879,592
Date of Patent: Mar. 9, 1999

[54] WATER SOLUBLE PHOTOCHROMIC COMPOUNDS, COMPOSITIONS AND OPTICAL ELEMENTS COMPRISING THE COMPOUNDS

[75] Inventor: Anil Kumar, Pittsburgh, Pa.

[73] Assignee: PPG Industries, Inc., Pittsburgh, Pa.

[21] Appl. No.: 988,310

[22] Filed: Dec. 10, 1997

[51] Int. Cl.⁶ .......................... C08K 5/15; C07D 311/92; C07D 311/04; G02B 5/23
[52] U.S. Cl. .................. 252/580; 359/642; 106/287.2; 549/389; 549/404; 549/48; 549/58; 549/60; 549/366; 546/165; 546/176; 546/196; 546/282.7; 548/444; 548/454
[58] Field of Search .......................... 252/586; 359/642; 351/163; 106/287.2; 549/389, 404, 48, 58, 60, 366; 546/165, 176, 196, 282.7; 548/444, 454

[56] References Cited

U.S. PATENT DOCUMENTS

| | | | |
|---|---|---|---|
| 3,562,172 | 2/1971 | Ono et al. | 252/300 |
| 3,567,605 | 3/1971 | Becker | 204/158 |
| 3,578,602 | 5/1971 | Ono et al. | 252/300 |
| 4,215,010 | 7/1980 | Hovey et al. | 252/300 |
| 4,342,668 | 8/1982 | Hovey et al. | 252/586 |
| 4,360,653 | 11/1982 | Stevens et al. | 526/301 |
| 4,816,584 | 3/1989 | Kwak et al. | 544/71 |
| 4,818,096 | 4/1989 | Heller et al. | 351/163 |
| 4,826,977 | 5/1989 | Heller et al. | 544/70 |
| 4,880,667 | 11/1989 | Welch | 427/160 |
| 4,931,219 | 6/1990 | Kwiatkowski | 252/586 |
| 4,994,208 | 2/1991 | McBain et al. | 252/586 |
| 5,066,818 | 11/1991 | Van Gemert et al. | 549/389 |
| 5,200,483 | 4/1993 | Selvig | 526/301 |
| 5,238,981 | 8/1993 | Knowles | 524/110 |
| 5,274,132 | 12/1993 | Van Gemert | 549/389 |
| 5,289,547 | 2/1994 | Ligas et al. | 382/7 |
| 5,350,775 | 9/1994 | Ohnishi et al. | 549/220 |
| 5,373,033 | 12/1994 | Toh et al. | 822/96 |
| 5,384,077 | 1/1995 | Knowles | 252/586 |
| 5,405,958 | 4/1995 | Van Gemert | 544/71 |
| 5,429,774 | 7/1995 | Kumar | 252/586 |
| 5,458,814 | 10/1995 | Kumar et al. | 252/586 |
| 5,466,398 | 11/1995 | Van Gemert et al. | 252/586 |
| 5,475,074 | 12/1995 | Matuoka et al. | 526/336 |
| 5,514,817 | 5/1996 | Knowles | 549/384 |
| 5,552,090 | 9/1996 | Van Gemert et al. | 252/586 |
| 5,552,091 | 9/1996 | Kumar | 252/586 |
| 5,565,147 | 10/1996 | Knowles et al. | 252/586 |
| 5,573,712 | 11/1996 | Kumar et al. | 252/586 |
| 5,574,049 | 11/1996 | Manley | 514/383 |
| 5,578,252 | 11/1996 | Van Gemert et al. | 252/586 |
| 5,645,767 | 7/1997 | Van Gemert | 252/586 |

FOREIGN PATENT DOCUMENTS 2670780  6/1992  France .
2 209 751  5/1989  United Kingdom .

OTHER PUBLICATIONS

Derwent Abstract of JP 48–023787, "Water Soluble Photochromic Compounds", (Mar. 1973).

Primary Examiner—John A. McPherson
Attorney, Agent, or Firm—Irwin M. Stein; Frank P. Mallak

[57] ABSTRACT

Described are novel water soluble photochromic naphthopyran and benzopyran compounds having an alkylaminoalkylamino group on the naphtho- or benzo-portions and/or pyran portions thereof. These compounds may be represented by one of the following graphic formulae:

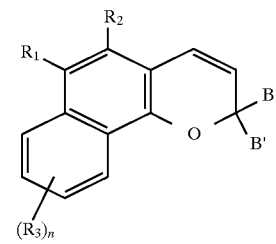

or

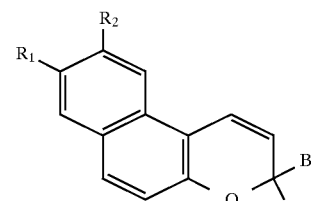

or

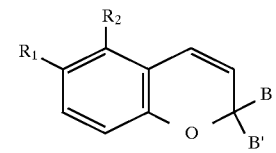

wherein $R_1$ is an alkylaminoalkylamino group. Articles such as ophthalmic lenses or other plastic transparencies and coating compositions such as paints and inks that incorporate the novel water soluble compounds are also described.

20 Claims, No Drawings

WATER SOLUBLE PHOTOCHROMIC COMPOUNDS, COMPOSITIONS AND OPTICAL ELEMENTS COMPRISING THE COMPOUNDS

DESCRIPTION OF THE INVENTION

The present invention relates to certain novel naphthopyran and benzopyran compounds. More particularly, this invention relates to novel photochromic water soluble naphthopyran and benzopyran compounds and to compositions and articles containing such novel water soluble compounds. When exposed to electromagnetic radiation containing ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −30° C. Irradiation of the compounds with visible light or upon raising the temperature to above about 0° C. is reported to reverse the coloration to a colorless state.

U.S. Pat. No. 5,458,814 describes photochromic 2,2-disubstituted-5,6-substituted-2H-naphtho[1,2-b]pyran compositions primarily for use in lenses and other plastic transparencies having an acceptable fade rate in addition to a high activated intensity and a high coloration rate. U.S. Pat. No. 5,466,398 discloses 3,3-disubstituted-8-substituted-3H-naphtho[2,1-b]pyran compositions for similar uses having additional substituents at the number 7 or number 9 carbon atom of the naphthopyran and which exhibit an improved solar response and higher activating wavelength than unsubstituted naphthopyrans.

U.S. Pat. No. 5,289,547 describes a method for authenticating articles wherein a photochromic compound is incorporated into ink which is printed or coated onto an article. The photochromic compound is dissolved in the ink in sufficient quantities to produce a visible display of a predetermined pattern or the like when the ink is illuminated by appropriate wavelengths of light.

The compounds disclosed in each of these patents are not water soluble, thus preparations thereof require is organic solvents. Many suitable organic solvents are hazardous materials requiring specialized handling and disposal procedures.

United Kingdom Patent Application GB 2209751A discloses a method of producing water soluble photochromic fulgides, fulgimides and adamantylidene spiropyrans by incorporating therein a sulphonic acid or chlorosulphonic acid group or acid salt. The photochromic compounds are sulphonated by treatment with sulphur trioxide or a dioxansulfur trioxide to impart water solubility thereto.

The present invention relates to novel water soluble photochromic compounds namely, certain 2H-naphtho[1,2-b]pyrans, 3H-naphtho[2,1-b]pyrans and benzopyrans each having at least one alkylaminoalkylamino group thereon. In an acidic environment, the alkylaminoalkylamino groups form quaternary salts, thereby rendering the photochromic compounds water soluble. These compounds have certain substituents on the pyran ring at the position ortho to the oxygen atom. Certain substituents are also present on the 2H-naphtho[1,2-b]pyran compounds at the number 5 and 6 carbon atoms of the naphtho portion of the naphthopyran, on the 3H-naphtho[2,1-b]pyran compounds at the number 8 and 9 carbon atoms of the naphtho portion of the naphthopyran and on the benzopyran compounds at the 5 and 6 carbon atoms.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-à-vis, glass lenses. Moreover, photochromic transparencies for vehicles, such as cars and airplanes, have been of interest because of the potential safety features that such transparencies offer.

Photochromic compounds are also useful in various non-ophthalmic articles such as inks, paints and coatings for security documents and decorative or fashion items. In particular, water soluble photochromic compounds possess processing and handling features not present in conventional water insoluble photochromic compounds.

In accordance with the present invention, it has been discovered that certain photochromic 2H-naphtho[1,2-b]pyrans, 3H-naphtho[2,1-b]pyrans and benzopyrans which are traditionally water insoluble may now be made water soluble by including thereon an alkylaminoalkylamino group. When acidified, the alkylaminoalkylamino group(s) forms quaternary ammonium salts rendering the compounds water soluble. These compounds may be described as 2H-naphtho[1,2-b]pyrans and 3H-naphtho[2,1-b]pyrans, each having certain substituents at the 2 position and the 3 position, respectively, of the pyran ring and an alkylaminoalkylamino group on the naphtho portion of the naphthopyran ring. The 2H-naphtho[1,2-b]pyrans and the 3H-naphtho[2,1-b]pyrans also have certain other substituents at the 5 position and the 9 position, respectively, on the naphtho portion of the naphthopyran ring. The compounds of the present invention also include benzopyrans having the same certain substituents at the 2 position of the pyran ring, certain other substituents at the 5 carbon atom and an alkylaminoalkylamino group at the 6 carbon atom of the benzopyran ring. The aforedescribed naphthopyrans and benzopyrans may be represented by the following graphic formulae I, II and III in which the numbers 1 through 10 in graphic formulae I and II identify the ring atoms of the naphthopyrans and the numbers 1 through 8 in the graphic formula III identify the ring atoms of the benzopyran. In the definition of the substituents shown in graphic formulae I, II and III, like symbols have the same meaning unless stated otherwise.

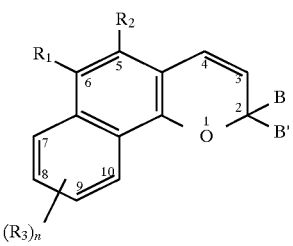

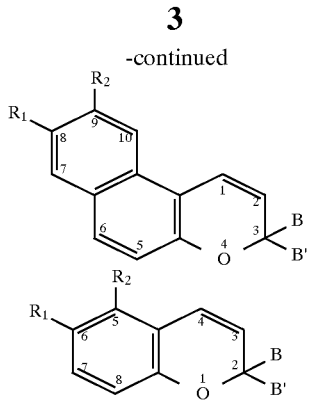

In graphic formulae I, II and III, $R_1$ is an alkylaminoalkylamino group represented by graphic formula IV:

wherein $R_4$ is $C_1$–$C_3$ alkyl, phenyl($C_1$–$C_3$)alkyl, phenyl or $R_5$, A is an anion, e.g., chloride, bromide, sulfate and phosphate.

In graphic formula IV, $R_5$ is a group represented by graphic formula V.

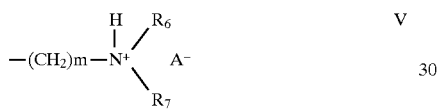

wherein $R_6$ and $R_7$ are each $C_1$–$C_3$ alkyl or $C_1$–$C_3$ alkylamino($C_1$–$C_3$)alkylamino and m is the integer 2, 3 or 4. Preferably, $R_4$ is methyl or 3-dimethylaminopropyl, and $R_6$ and $R_7$ are each methyl and m is 2, 3 or 4; most preferably m is 3.

$R_2$ in graphic formulae I, II and III is the group, —C(O)W or —CH$_2$OH, W being —OR$_8$ or —N(R$_9$)R$_{10}$, wherein $R_8$ is hydrogen, allyl, $C_1$–$C_6$ alkyl, e.g., methyl, ethyl, propyl, butyl, pentyl, and hexyl, phenyl, mono($C_1$–$C_6$)alkyl substituted phenyl, mono($C_1$–$C_6$)alkoxy-substituted phenyl, phenyl($C_1$–$C_3$)alkyl, mono($C_1$–$C_3$)alkoyl substituted phenyl ($C_1$–$C_3$)alkyl, $C_1$–$C_6$ alkoxy($C_2$–$C_4$)alkyl, or $C_1$–$C_6$ haloalkyl; and $R_9$ and $R_{10}$ may each be selected from the group consisting of hydrogen, $C_1$–$C_6$ alkyl, $C_5$–$C_7$ cycloalkyl, phenyl and mono- or di-substituted phenyl. The phenyl substituents may be $C_1$–$C_6$ alkyl and $C_1$–$C_6$ alkoxy and the halo substituents may be chloro or fluoro.

More preferably, $R_2$ is the group, —C(O)W, W being the groups —OR$_8$ or —N(R$_9$)R$_{10}$, wherein $R_8$ is hydrogen, $C_1$–$C_4$ alkyl, phenyl, mono($C_1$–$C_4$)alkyl substituted phenyl, mono($C_1$–$C_4$)alkoxy substituted phenyl, phenyl($C_1$–$C_2$) alkyl, mono($C_1$–$C_4$)alkyl substituted phenyl($C_1$–$C_2$)alkyl, mono($C_1$–$C_4$)alkoxy substituted phenyl($C_1$–$C_2$)alkyl, mono ($C_1$–$C_4$)alkoxy($C_2$–$C_3$)alkyl, or $C_1$–$C_4$ haloalkyl; and $R_9$ and $R_{10}$ may each be selected from the group consisting of hydrogen, $C_1$–$C_4$ alkyl, $C_5$–$C_7$ cycloalkyl, phenyl and mono- or di-substituted phenyl. The phenyl substituents may be selected from $C_1$–$C_4$ alkyl and $C_1$–$C_4$ alkoxy, and the halo substituents may be chloro or fluoro. Most preferably, $R_2$ is the group —C(O)W, W being the group —OR$_8$, wherein $R_8$ is a $C_1$–$C_3$ alkyl.

Each $R_3$ in graphic formula I is $C_1$–$C_6$ alkyl, $C_3$–$C_7$ cycloalkyl, substituted or unsubstituted phenyl, or the group —OR$_{11}$, wherein $R_{11}$ is hydrogen or $C_1$–$C_6$ alkyl, said phenyl substituents each being selected from $C_1$–$C_6$ alkyl or $C_1$–$C_6$ alkoxy, and n is the integer 0, 1 or 2. Preferably, each $R_3$ is $C_1$–$C_3$ alkyl, $C_3$–$C_5$ cycloalkyl, substituted or unsubstituted phenyl or —OR$_{11}$, wherein $R_{11}$ is hydrogen or $C_1$–$C_3$ alkyl, said phenyl substituents each being $C_1$–$C_3$ alkyl or $C_1$–$C_3$ alkoxy and n is the integer 0 or 1.

B and B' in graphic formulae I, II and III may each be selected from the group consisting of:

(i) the unsubstituted, mono-, di- and tri-substituted aryl groups, phenyl and naphthyl;

(ii) the unsubstituted, mono- and di-substituted heteroaromatic groups pyridyl, furanyl, benzofuran-2-yl, benzofuran-3-yl, thienyl, benzothien-2-yl, benzothien-3-yl, dibenzofuranyl, dibenzothienyl, carbazolyl and fluorenyl, each of said aryl and heteroaromatic substituents in parts (i) and (ii) being selected from the group consisting of hydroxy, aryl, mono($C_1$–$C_6$) alkoxyaryl, di($C_1$–$C_6$)alkoxyaryl, mono($C_1$–$C_6$) alkylaryl, di($C_1$–$C_6$)alkylaryl, bromoaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$) alkyl, $C_3$–$C_7$ cycloalkyloxy($C_1$–$C_6$)alkoxy, aryl ($C_1$–$C_6$)alkyl, aryl($C_1$–$C_6$)alkoxy, aryloxy, aryloxy ($C_1$–$C_6$)alkyl, aryloxy($C_1$–$C_6$)alkoxy, mono- and di($C_1$–$C_6$)alkylaryl($C_1$–$C_6$)alkyl, mono- and di($C_1$–$C_6$) alkoxyaryl($C_1$–$C_6$)alkyl, mono- and di($C_1$–$C_6$) alkylaryl($C_1$–$C_6$)alkoxy, mono- and di($C_1$–$C_6$) alkoxyaryl($C_1$–$C_6$)alkoxy, amino, mono($C_1$–$C_6$) alkylamino, di($C_1$–$C_6$)alkylamino, diarylamino, N-($C_1$–$C_6$)alkylpiperazino, N-arylpiperazino, aziridino, indolino, piperidino, arylpiperidino, morpholino, thiomorpholino, tetrahydroquinolino, tetrahydroisoquinolino, pyrryl, $C_1$–$C_6$ alkyl, $C_1$–$C_6$ bromoalkyl, $C_1$–$C_6$ chloroalkyl, $C_1$–$C_6$ fluoroalkyl, $C_1$–$C_6$ alkoxy, mono($C_1$–$C_6$)alkoxy($C_1$–$C_4$)alkyl, acryloxy, methacryloxy, bromo, chloro and fluoro;

(iii) the groups represented by the following graphic formulae:

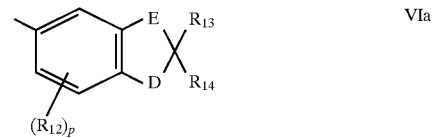

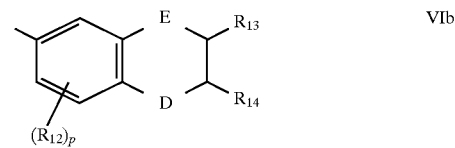

wherein E may be carbon or oxygen and D may be oxygen or substituted nitrogen, provided that when D is substituted nitrogen, E is carbon, said nitrogen substituents being selected from the group consisting of hydrogen, $C_1$–$C_6$ alkyl and $C_2$–$C_6$ acyl; each $R_{12}$ is $C_1$–$C_6$ alkyl, $C_1$–$C_6$ alkoxy, hydroxy, bromo, chloro or fluoro; $R_{13}$ and $R_{14}$ are each hydrogen or $C_1$–$C_6$ alkyl; and p is the integer 0, 1 or 2;

(iv) $C_1$–$C_6$ alkyl, $C_1$–$C_6$ bromoalkyl, $C_1$–$C_6$ chloroalkyl, $C_1$–$C_6$ fluoroalkyl, $C_1$–$C_6$ alkoxy($C_1$–$C_4$)alkyl, $C_3$–$C_6$ cycloalkyl, mono($C_1$–$C_6$)alkoxy($C_3$–$C_6$)cycloalkyl, mono($C_1$–$C_6$)alkyl($C_3$–$C_6$)cycloalkyl, bromo($C_3$–$C_6$) cycloalkyl, chloro($C_3$–$C_6$)cycloalkyl and fluoro ($C_3$–$C_6$)cycloalkyl; and (v) the group represented by the following graphic formula:

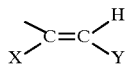

VIc wherein X in graphic formula VIc may be hydrogen or $C_1$–$C_4$ alkyl and Y in graphic formula VIc may be selected from the unsubstituted, mono-, and di-substituted members of the group consisting of naphthyl, phenyl, furanyl and thienyl, each of said group substituents in this part (v) being $C_1$–$C_4$ alkyl, $C_1$–$C_4$ alkoxy, bromo, fluoro or chloro; or (vi) B and B' taken together form fluoren-9-ylidene, mono- or di-substituted fluoren-9-ylidene or form a member selected from the group consisting of saturated $C_3$–$C_{12}$ spiro-monocyclic hydrocarbon rings, e.g., cyclopropylidene, cycloheptylidene, cyloocntylidene, cyclononylidene, cyclodecylidene cycloundecylidene and cyclododecylidene; cyclodecylidene cycloundecylidene and cyclododecylidene; saturated $C_7$–$C_{12}$ spiro-bicyclic hydrocarbon rings, e.g., bicyclo[2.2.1] heptylidene, i.e., norbornylidene, 1,7,7-trimethyl bicyclo[2.2.1]heptylidene, i.e., bornylidene, bicyclo [3.2.1]octylidene, bicyclo[3.3.1]nonan-9-ylidene and bicyclo[4.3.2]undecane and saturated $C_7$–$C_{12}$ spiro-tricyclic hydrocarbon rings, e.g., tricyclo[$2.2.1.0^{2,6}$] heptylidene and tricyclo[$3.3.1.1^{3,7}$]decylidene, i.e., adamantylidene, and tricyclo[$5.3.1.1^{2,6}$]dodecylidene, each of said fluoren-9-ylidene substituents being selected from the group consisting of $C_1$–$C_4$ alkyl, $C_1$–$C_4$ alkoxy, bromo, fluoro and chloro.

More preferably, B and B' are each selected from the group consisting of: (i) phenyl, mono-substituted phenyl and di-substituted phenyl, preferably substituted in the meta and/or para positions; (ii) the unsubstituted, mono- and di-substituted heteroaromatic groups furanyl, benzofuran-2-yl, thienyl, benzothien-2-yl, dibenzofuran-2-yl and dibenzothien-2-yl, each of said phenyl and heteroaromatic substituents in (i) and (ii) being selected from the group consisting of hydroxy, aryl, aryloxy, aryl($C_1$–$C_3$)alkyl, amino, mono($C_1$–$C_3$)alkylamino, di($C_1$–$C_3$)alkylamino, N-($C_1$–$C_3$)alkylpiperazino, indolino, piperidino, morpholino, pyrryl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$)alkoxy($C_1$–$C_3$) alkyl, fluoro and chloro; (iii) the groups represented by the graphic formulae VIa and VIb, wherein E is carbon and D is oxygen, $R_{12}$ is $C_1$–$C_3$ alkyl or $C_1$–$C_3$ alkoxy, $R_{13}$ and $R_{14}$ are each hydrogen or $C_1$–$C_4$ alkyl; and p is the integer 0 or 1; (iv) $C_1$–$C_4$ alkyl; and (v) the group represented by the graphic formula VIc wherein X is hydrogen or methyl and Y is phenyl or mono-substituted phenyl, said phenyl substituent being selected from the group consisting of $C_1$–$C_3$ alkyl, $C_1$–$C_3$ alkoxy and fluoro; or (vi) B and B' taken together form fluoren-9-ylidene, mono-substituted fluoren-9-ylidene or a member selected from the group consisting of saturated $C_3$–$C_8$ spiro-monocyclic hydrocarbon saturated $C_7$–$C_{10}$ spiro-tricyclic hydrocarbon rings, sand fluoren-9-ylidene substituent being selected from the group consisting of $C_1$–$C_3$ alkyl, $C_1$–$C_3$ alkoxy, fluoro and chloro.

Most preferably, B and B' are each selected from the group consisting of (i) phenyl, mono- and di-substituted phenyl; (ii) the unsubstituted, mono- and di-substituted heteroaromatic groups furanyl, benzofuran-2-yl, thienyl and benzothien-2-yl, each of said phenyl and heteroaromatic substituents in (i) and (ii) being selected from the group consisting of hydroxy, $C_1$–$C_3$ alkyl, $C_1$–$C_3$ alkoxy, aryl, morpholino, fluoro and chloro; and (iii) the group represented by graphic formula VIa, wherein E is carbon and D is oxygen, $R_{12}$ is $C_1$–$C_3$ alkyl or $C_1$–$C_3$ alkoxy, $R_{13}$ and $R_{14}$ are each hydrogen or $C_1$–$C_3$ alkyl, and p is the integer 0 or 1; or (iv) B and B' taken together form fluoren-9-ylidene, adamantylidene, bornylidene, norbornylidene or bicyclo [3.3.1]nonan-9-ylidene.

Compounds represented by graphic formula I may be prepared by the following steps. In Reaction A, an alkyl magnesium halide reagent is reacted with a secondary amine corresponding to the $R_1$ group in graphic formulae I, II and III and represented by graphic formula VII in the presence of tetrahydrofuran (THF) to form the corresponding halomagnesium amide represented by graphic formula VIII wherein Z is a halide including bromide, chloride and iodide.

Reaction A

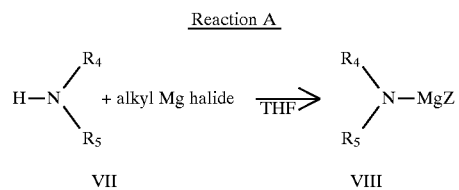

VII                VIII

In Reaction B, the halomagnesium amide represented by graphic formula VIII is reacted with the 2H-naphtho[1,2-b] pyran represented by graphic formula IX in the presence of THF and quenched with water to form compounds represented by graphic formula Ia. In graphic formula IX, $R_{11}$ is methyl. The compound represented by graphic formula IX may be prepared by coupling a substituted naphthol with a propargyl alcohol. This procedure is described in U.S. Pat. No. 5,458,814, column 5, line 10 to column 7, line 67. The propargyl alcohol may be prepared according to the methods disclosed in U.S. Pat. No. 5,645,767, column 5, line 8 to column 6, line 30. The aforesaid patents are incorporated herein in toto by reference.

Reaction B

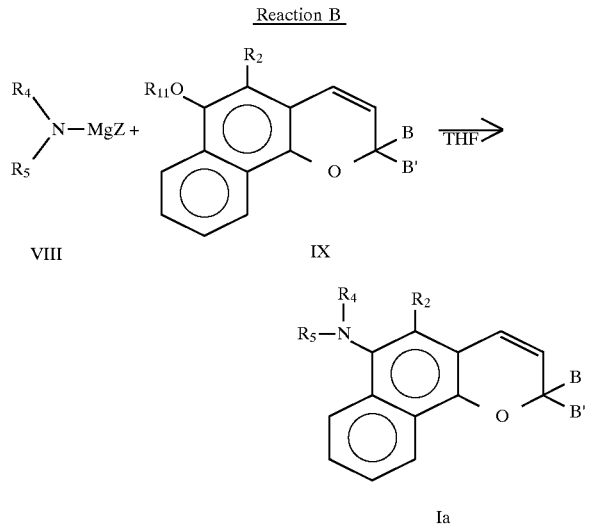

VIII                IX

Ia

As shown in Reaction C, when $R_2$ is methoxycarbonyl, the compounds represented by graphic formula Ia may be reduced by reaction thereof with a reagent, preferably lithium aluminum hydride, in THF to form the compounds represented by graphic formula Ib. The free base compounds represented by graphic formulae Ia and Ib are acidified to produce the corresponding quaternary ammonium salts which are water soluble.

Reaction C

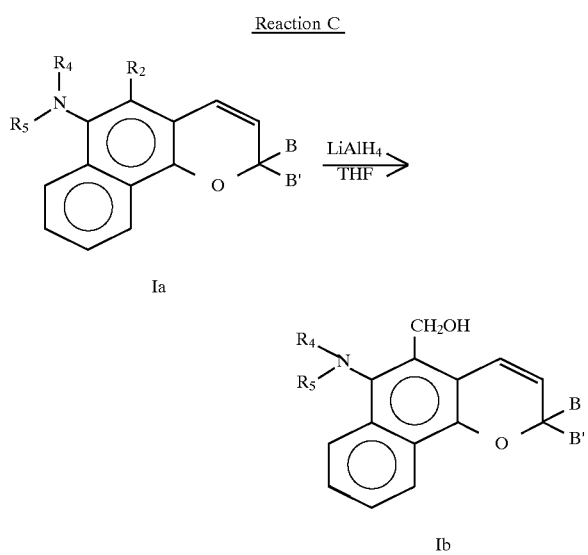

Examples of the free base of contemplated 2H-naphtho[1,2-b]pyrans within the scope of the invention are the following:

(a) 2,2-bis(4-methoxyphenyl)-5-methoxycarbonyl-6-bis(3-dimethylaminopropyl)amino-2H-naphtho[1,2-b]pyran;

(b) 2,2-diphenyl-5-methoxycarbonyl-6-(3-dimethylaminopropyl)methylamino-2H-naphtho[1,2-b]pyran; and (c) 2,2-diphenyl-5-methylol-6-(3-dimethylaminopropyl)methylamino-2H-naphtho[1,2-b]pyran.

Compounds represented by graphic formula II may be prepared by first following Reaction A to produce the halomagnesium amide represented by graphic formula VIII. In reaction D, the 3H-naphtho[2,1-b]pyran represented by graphic formula X is reacted with the halomagnesium amide represented by graphic formula VIII in the presence of THF and quenched with water to form compounds represented by graphic formula IIa. In graphic formula X, $R_{11}$ is methyl. The compound represented by graphic formula X may be prepared by coupling methyl-3,7-dihydroxy-2-naphthoate with propargyl alcohol. This procedure is disclosed in U.S. Pat. No. 5,466,398, column 3, line 65 to column 9, line 28, incorporated herein in toto by reference. The propargyl alcohol may be prepared according to the methods disclosed in U.S. Pat. No. 5,645,767. The compounds represented by graphic formula IIa are acidified to produce the corresponding quaternary ammonium salts which are water soluble.

Reaction D

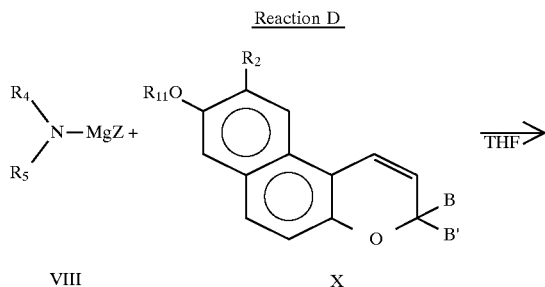

Reaction D -continued

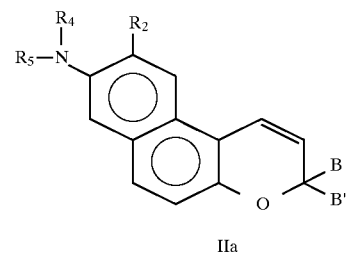

Examples of the free base form of contemplated [3H]-naphtho[2,1-b]pyrans within the scope of the invention are the following:

(a) 3,3-bis(4-methoxyphenol)-8-bis(3-dimethyl aminopropyl)amino-3H-naphtho[2,1-b]pyran; and (b) 3,3-diphenyl-8-(3-dimethylaminopropyl)methylamino-3H-naphtho[2,1-b]pyran.

Compounds represented by graphic formula III may be prepared by first following Reaction A to produce the halomagnesium amide represented by graphic formula VIII. In Reaction E, the dihydroxybenzoic acid represented by graphic formula XI is reacted with an alkyl halide or a benzylhalide, e.g., methyl iodide, ethyl chloride, benzyl bromide, etc., (R" halide) in the presence of ethyldiisopropyl amine or sodium bicarbonate in a suitable solvent such as anhydrous dimethylformamide (DMF) to form the corresponding dihydroxybenzoate represented by graphic formula XII.

Reaction E

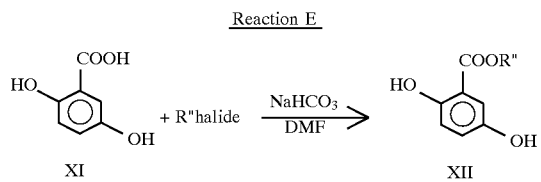

In Reaction F, propargyl alcohol represented by graphic formula XIII having the B and B' substituents defined above for graphic formulae I, II and III is coupled with the dihydroxybenzoate represented by graphic formula XII in the presence of p-toluene sulfonic acid (PTSA) in a suitable solvent such as toluene to produce benzopyrans represented by graphic formula XIV. The propargyl alcohol represented by graphic formula XIII may be prepared according to the method described in U.S. Pat. No. 5,645,767, column 5, line 8 to column 6, line 30. The benzopyrans represented by graphic formula XIV are alkylated, via, e.g., reaction with methyl iodide in the presence of anhydrous potassium carbonate in a suitable solvent such as anhydrous acetone to form the alkoxy substituted benzopyran compounds represented by graphic formula XV. Alkylating reactions are further described in *Organic Synthesis*, Vol. 31, pages 90–93, John Wiley and Sons, Inc., New York, N.Y. (1951).

Reaction F

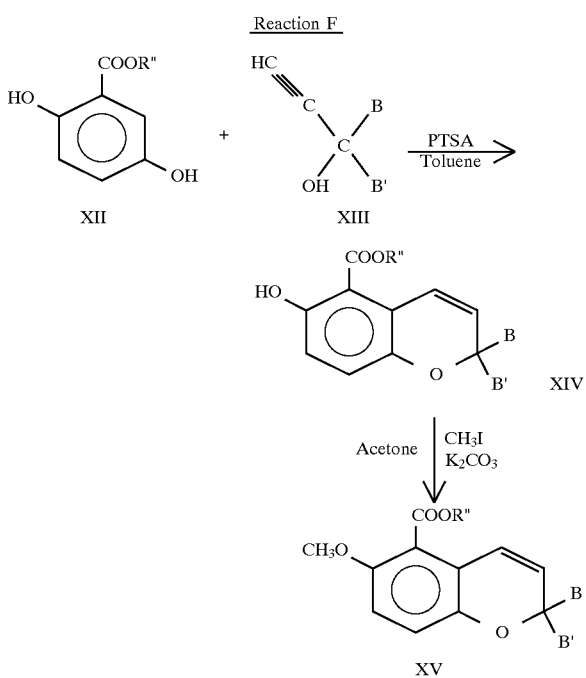

In Reaction G, the benzopyran represented by graphic formula XV is reacted with the halomagnesium amide represented by graphic formula VIII in the presence of THF and quenched with water to form compounds represented by graphic formula IIIA. The alkoxycarbonyl group (—COOR") in graphic formula IIIA may be reduced by reaction with a reagent, preferably, lithium aluminum hydride, in THF to form the corresponding hydroxy compounds. The compounds represented by graphic formula IIIA are acidified to form the corresponding quaternary ammonium salts which are water soluble.

Reaction G

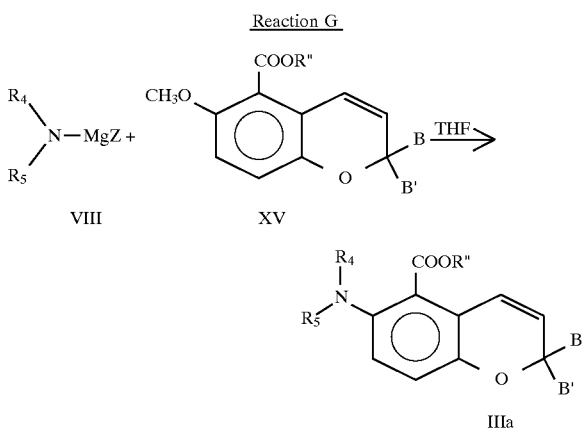

An example of the free base form of a contemplated benzopyran within the scope of the invention is 2,2-diphenyl-5-methoxycarbonyl-6-bis(3-dimethylaminopropyl)amino-2H-benzopyran.

Aqueous solutions of the inventive photochromic compounds may be used to incorporate the compounds into an article. The water solubility of the naphthopyrans and benzopyrans of the present invention depends on the ratio of the number of hydrophilic moieties to the number of hydrophobic moieties thereon. The quaternary ammonium salt of the amino functionality identified as the $R_1$ substituent on these compounds is hydrophilic. By water soluble it is meant that a measurable amount of the photochromic compounds of the present invention is soluble in water. The compounds of the present invention having only two quaternary ammonium salt functionalities in the $R_1$ group are soluble in water at about 1 gram per liter. It is contemplated that the inventive compounds having more than two quaternary ammonium salt functionalities in the $R_1$ group are more water soluble. Thus, the compounds of the present invention are at least water soluble at one gram per liter. The present invention further includes the corresponding free bases of the quaternary ammonium salts represented by graphic formulae I, II and III.

The water soluble compounds represented by graphic formulae I, II and III may be used in those applications in which organic photochromic substances may be employed, such as optical lenses, e.g., vision correcting ophthalmic lenses and plano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions. Coating compositions are defined herein to include paints, i.e., a pigmented liquid or paste used for the decoration, protection and/or the identification of a substrate, and inks, i.e., a pigmented liquid or paste used for writing and printing on substrates. Substrates are materials to which the coating composition is applied, of any type such as, paper, glass, ceramics, wood, masonry, textiles, metals and organic polymeric materials. Coating compositions may be used to produce verification marks on security documents, e.g., documents such as banknotes, passport and drivers' licenses for which authentication or verification of authenticity may be desired. The water soluble photochromic compounds of the present invention may also be used as tracers, e.g., in flow studies by injecting the inventive compounds into a portion of an aqueous flow system, exposing the flow system to the appropriate UV light which will induce a color change in the inventive compounds and monitoring their distribution in the flow system.

The 2H-naphtho-[1,2-b]pyrans represented by graphic formula I exhibit color changes from colorless to colors ranging from yellow to red/purple. The 3H-naphtho[2,1-b] pyrans represented by graphic formula II exhibit color changes from colorless to colors ranging from yellow to orange and red. The benzopyrans represented by graphic formula III exhibit color changes from colorless to colors ranging from red to purple.

It is contemplated that the photochromic naphthopyrans and benzopyrans of the present invention may each be used alone in the acid salt form, in combination with the acid salts of other naphthopyrans and benzopyrans of the present invention, or as the corresponding free bases in combination with one or more other appropriate complementary organic photochromic materials, i.e., organic photochromic compounds having at least one activated absorption maxima within the range of between about 400 and 700 nanometers (or substances containing the same) and which color when activated to an appropriate hue. The photochromic compounds of the present invention may be associated with, incorporated in, e.g., dissolved or dispersed in, a polymeric organic host material used to prepare photochromic articles.

Other than where otherwise indicated, all numbers expressing wavelengths, quantities of ingredients or reaction conditions used herein are to be understood as modified in all instances by the term "about".

Examples of complementary organic photochromic compounds include indenonaphthopyrans, chromenes and oxazines, naphthopyrans, substituted 2H-phenanthro[4,3-b] pyran and 3H-phenanthro[1,2-b]pyran compounds, other benzopyran compounds having substituents at the 2-position of the pyran ring and mixtures of such photochromic compounds. Many of such photochromic compounds are described in the open literature, e.g., U.S. Pat. Nos. 3,562, 172; 3,567,605; 3,578,602; 4,215,010; 4,342,668; 4,816, 584; 4,818,096; 4,826,977; 4,880,667; 4,931,219; 5,066, 818; 5,238,981; 5,274,132; 5,384,077; 5,405,958; 5,429, 774; 5,458,814, 5,466,398; 5,514,817; 5,552,090; 5,552, 091; 5,565,147; 5,573,712; 5,578,252; WO 96 14596 and Japanese Patent Publication 62/195383. Spiro(indoline) pyrans are also described in the text, *Techniques in Chemistry*, Volume III, "Photochromism", Chapter 3, Glenn H. Brown, Editor, John Wiley and Sons, Inc., New York, 1971.

The disclosures relating to such photochromic compounds in the aforedescribed patents are incorporated herein, in toto, by reference. The photochromic articles of the present invention may contain one photochromic compound or a mixture of photochromic compounds, as desired.

Each of the photochromic substances described herein may be used in amounts (or in a ratio) such that an organic host material to which the photochromic compounds or mixture of compounds is applied or in which they are incorporated exhibits a desired resultant color, e.g., a substantially neutral color when activated with unfiltered sunlight, i.e., as near a neutral color as possible given the colors of the activated photochromic compounds. Neutral gray and neutral brown colors are preferred.

A neutral gray color exhibits a spectrum that has relatively equal absorption in the visible range between 400 and 700 nanometers. A neutral brown color exhibits a spectrum in which the absorption in the 400–550 nanometer range is moderately larger than in the 550–700 nanometer range. An alternative way of describing color is in terms of its chromaticity coordinates, which describe the qualities of a color in addition to its luminance factor, i.e., its chromaticity. In the CIE system, the chromaticity coordinates are obtained by taking the ratios of the tristimulus values to their sum, e.g., x=X/(X+Y+Z) and y=Y/(X+Y+Z). Color as described in the CIE system can be plotted on a chromaticity diagram, usually a plot of the chromaticity coordinates x and y. See pages 47–52 of *Principles of Color Technology*, by F. W. Billmeyer, Jr., and Max Saltzman, Second Edition, John Wiley and Sons, N.Y. (1981). As used herein, a near neutral color is one in which the chromaticity coordinate values of "x" and "y" for the color are within the following ranges (D65 illuminant): x=0.260 to 0.400, y=0.280 to 0.400 following activation to 40 percent luminous transmission by exposure to solar radiation (Air Mass 1 or 2).

The amount of the photochromic naphthopyrans and/or benozpyrans to be applied to or incorporated into a carrier or host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic compounds. Typically, the more photochromic compound applied or incorporated, the greater is the color intensity up to a certain limit.

The relative amounts of the aforesaid photochromic compounds used will vary and depend in part upon the relative intensities of the color of the activated species of such compounds, and the ultimate color desired. Generally, the amount of total photochromic compound incorporated into or applied to a photochromic optical host material may range from about 0.05 to about 1.0, e.g., from 0.1 to about 0.45, milligrams per square centimeter of volume or surface to which the photochromic compounds is incorporated or applied.

The photochromic naphthopyrans and benzopyrans of the present invention may be associated with, applied to or incorporated within the host material by various methods described in the art. Such methods include dissolving or dispersing the photochromic compounds in water or organic polymeric host material, e.g., casting it in place by adding the photochromic compounds to the monomeric host material prior to polymerization; imbibition of the photochromic compounds into the host material by immersion of the host material in a hot solution of the photochromic compounds or by thermal transfer; providing the photochromic compounds as a separate layer between adjacent layers of the host material, e.g., as a part of a polymeric film; and applying the photochromic compounds as part of a coating placed on the surface of the host material. The term "imbibition" or "imbibe" is intended to mean and include permeation of the photochromic compounds alone into the host material, solvent assisted transfer of the photochromic compounds into a porous polymer, vapor phase transfer, and other such transfer mechanisms.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic compounds, e.g., to achieve a more neutral color or absorb a particular wavelength of incident light. In another embodiment, the dye may be selected to provide a desired hue to the host material when the photochromic compounds are in an unactivated state.

The host material will usually be transparent, but may be translucent or even opaque. The host material need only be pervious to that portion of the electromagnetic spectrum, which activates the photochromic substance, i.e., that wavelength of ultraviolet (UV) light that produces the open or colored form of the substance and that portion of the visible spectrum that includes the absorption maximum wavelength of the substance in its UV activated form, i.e., the open form. Preferably, the host color should not be such that it masks the color of the activated form of the photochromic compounds, i.e., so the change in color is readily apparent to the observer.

The photochromic compounds of the present invention are soluble in water when acidified to form quaternary salts. Aqueous solutions of the quaternary salts of the photochromic compounds may be used to disperse the photochromic compounds into an organic polymeric host material or other materials such as textiles and ink or paint bases. Alternatively, the free base form of the photochromic compounds may be dissolved in an organic solvent. The organic solvent may be selected from the group consisting of benzene, toluene, methyl ethyl ketone, acetone, ethanol, tetrahydrofurfuryl alcohol, N-methyl pyrrolidinone, 2-methoxyethyl ether, xylene, cyclohexane, 3-methyl cyclohexanone, ethyl acetate, tetrahydrofuran, methanol, methyl propitiate, ethylene glycol and mixtures thereof. Preferably, the organic solvent is selected from the group consisting of acetone, ethanol, tetrahydrofurfuryl alcohol, 2-methoxyethyl ether, 3-methyl cyclohexanone, N-methyl pyrrolidinone and mixtures thereof. Preferably, the organic polymeric host material is a solid transparent or optically clear material, e.g., materials suitable for optical applications, such as plano and ophthalmic lenses, windows, automotive transparencies, e.g., windshields, aircraft transparencies, plastic sheeting, polymeric films, etc. Examples of polymeric organic host materials are polymers prepared from individual monomers or mixtures of monomers selected from the following groups:

(a) diacrylate or dimethacrylate compounds represented by graphic formula XVI:

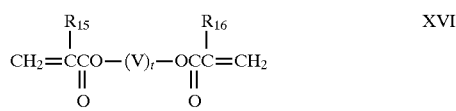

wherein $R_{15}$ and $R_{16}$ may be the same or different and are hydrogen or methyl, and V is methylene ($CH_2$) and t is an integer of from 1 to 20;

(b) diacrylate or dimethacrylate compounds represented by graphic formula XVII:

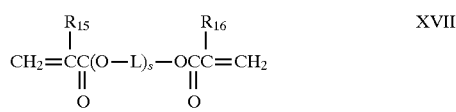

wherein L is $CH_2CH(R_{16})$, or $(CH_2)_v$, wherein v is an integer selected from the group consiting of 1, 3 and 4, and s is an integer of from 1 to 50; and (c) an acrylate or a methacrylate compound having an epoxy group represented by graphic formula XVIII:

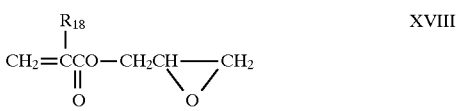

wherein $R_{18}$ is hydrogen or methyl.

In graphic formulae XVI, XVII and XVIII, like letters used with respect to the definitions of different substituents have the same meaning.

Examples of diacrylate or dimethacrylate compounds represented by graphic formulae XVI include butanediol di(meth)acrylate, hexanediol di(meth)acrylate and nonanediol di(meth)acrylate, and represented by graphic formula XVII include diethylene glycol dimethacrylate, triethylene glycol dimethacrylate, etc., butanediol dimethacrylate and poly(oxyalkylene dimethacrylates), e.g., polyethylene glycol (600) dimethacrylate. Examples of acrylate or methacrylate compounds represented by graphic formula XVIII include glycidyl acrylate and glycidyl methacrylate.

Further examples of polymeric organic host materials which may be used with the photochromic compounds described herein include: polymers, i.e., homopolymers and copolymers, of the monomers and mixtures of monomers represented by graphic formulae XVI, XVII and XVIII, bis(allyl carbonate) monomers, diisopropenyl benzene monomers, ethoxylated bisphenol A dimethacrylate monomers, ethylene glycol bismethacrylate monomers, poly (ethylene glycol) bismethacrylate monomers, ethoxylated phenol bismethacrylate monomers, alkoxylated polyhydric alcohol polyacrylate monomers, such as ethoxylated trimethylol propane triacrylate monomers, urethane acrylate monomers, such as those described in U.S. Pat. No. 5,373, 033, and vinylbenzene monomers, such as those described in U.S. Pat. No. 5,475,074 and styrene; polymers, i.e., homopolymers and copolymers, of polyfunctional, e.g., mono-, di- or multi-functional, acrylate and/or methacrylate monomers, poly($C_1$–$C_{12}$ alkyl methacrylates), such as poly (methyl methacrylate), poly(alkoxylated phenol methacrylates), cellulose acetate, cellulose triacetate, cellulose acetate propionate, cellulose acetate butyrate, poly[]vinyl acetate), poly(vinyl alcohol), poly(vinyl chloride), poly(vinylidene chloride), polyurethanes, thermoplastic polycarbonates, polyesters, poly(ethylene terephthalate), polystyrene, poly(alpha methylstyrene), copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers, e.g., ethyl acrylate, butyl acrylate.

Transparent copolymers and blends of transparent polymers are also suitable as host materials. Preferably, the host material is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis (allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483; poly(vinyl acetate), polyvinylbutyral, polyurethane, polymers of members of the group consisting of diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile.

More particularly, contemplated is use of the photochromic naphthopyrans and benzopyrans of the present invention with optical organic resin monomers used to produce optically clear polymerizates, i.e., materials suitable for optical applications, such as for example plano and ophthalmic lenses, windows, and automotive transparencies. Such optically clear polymerizates may have a refractive index that may range from about 1.48 to about 1.75, e.g., from about 1.495 to about 1.66. Specifically contemplated are optical resins sold by PPG Industries, Inc. under the CR-designation, e.g., CR-307 and CR-407.

The water soluble photochromic compounds of the present invention offer handling and processing advantages not achieved by water insoluble photochromic compounds. In particular, the use of hazardous organic solvents as carriers for photochromic compounds is avoided. As a final step in the preparation of optical lenses and other transparent polymeric articles, the surfaces thereof must be cleaned of excess photochromic compounds. Because the photochromic compounds of the present invention are water soluble in an acidic environment, such surfaces may be cleaned with a dilute acid.

It is further contemplated that the photochromic naphthopyrans and benzopyrans of the present invention may be used in aqueous or organic based inks or paints. The inventive photochromic compounds may be incorporated into different printing inks and paints for application on various articles including printed documents, printed textiles, and painted or coated articles for functional or decorative purposes. Hereafter, by the term ink it is meant all inks, paints and the like for application to another article or incorporation into another composition. The inventive photochromic compounds should (a) provide a measurable photochromic response when incorporated into an ink and exposed to a source of activating light, (b) be soluble within the ink and (c) be chemically compatible with the base ink composition.

Although the present invention has been described with respect to photochromic 2H-naphtho[1,2-b]pyrans, 3H-naphtho[2,1-b]pyrans and benzopyrans, other related photochromic compounds could be made water soluble via amination in a similar manner. Such other related photochromic compounds include compounds having an alkoxy group at a position ortho to an ester substituent suitable for coupling with a halomagnesium amide and subsequent acidification thereof to produce a water soluble aminosubstituted photochromic compound.

The present invention is more particularly described in the following examples which are intended as illustrative only, since numerous modifications and variations therein will be apparent to those skilled in the art.

EXAMPLE 1

Step 1

Bis(3-dimethylaminopropyl)amine (4 grams) was added to a reaction flask containing 50 milliliters (mL) of anhydrous tetrahydrofuran (THF) and stirred at room temperature. Methyl magnesium bromide in a stoichiometric amount (7 mL of a 3 molar hexane solution) was added and stirred for one hour. The reaction mixture containing bromomagnesium bis(3-dimethylaminopropyl)amide was not purified but used directly in the next step.

Step 2

2,2-bis(4-methoxyphenyl)-5-methoxycarbonyl-6-methoxy-2H-naphtho[1,2-b]pyran (3 grams) was added to a flask containing anhydrous tetrahydrofuran (5 mL). The naphthopyran solution was added to the reaction mixture of Step 1 and stirred at room temperature for two hours. Water (100 mL) was slowly added and stirred for one half hour. The resulting mixture was extracted three times with diethyl ether (25 mL each). The three organic extracts were combined and washed with distilled water. The resulting diethyl ether solution was extracted three times with a 10 weight percent hydrochloric acid solution (25 mL each). The three acid solutions were combined and neutralized with a 10 weight percent sodium hydroxide solution. The resulting neutral solution was extracted three times with diethyl ether (25 mL each). The three organic extracts were combined, washed with water and dried over anhydrous magnesium sulfate. The solvent was evaporated leaving 2 grams of an oily product. A nuclear magnetic resonance (NMR) spectrum showed the product to have a structure consistent with 2,2-bis(4-methoxyphenyl)-5-methoxycarbonyl-6-bis(3-dimethylaminopropyl)amino-2H-naphtho[1,2-b]pyran.

Step 3

The 2,2-bis(4-methoxyphenyl)-5-methoxycarbonyl-6-bis(3-dimethylaminopropyl)amino-2H-naphtho[1,2-b]pyran prepared in Step 2 was added to a reaction flask containing anhydrous diethyl ether. The solution was bubbled with dry hydrochloric acid gas until a white solid separated out. The solid was removed from the solution by filtration, washed with anhydrous diethyl ether, washed with hexane, dried and was determined to have a water solubility of 1 gram per liter. Upon acidification and illumination with ultraviolet light, an aqueous solution of the product exhibited a red-purple color.

EXAMPLE 2

Step 1

The procedure of Step 1 of Example 1 was followed except that N,N',N'-trimethyl-1,3-propanediamine was used in place of bis(3-dimethylaminopropyl)amine to produce a reaction mixture containing bromomagnesium N,N',N'-trimethyl-1,3-propanediamide.

Step 2

2,2-diphenyl-5-methoxycarbonyl-6-methoxy-2H-naphtho[1,2-b]pyran (3 grams) was added to a flask containing anhydrous tetrahydrofuran (10 mL). The resulting naphthopyran solution was added to the reaction mixture of Step 1 and stirred at room temperature for two hours. Water (100 mL) was added to the reaction mixture and the resulting mixture was extracted three times with diethyl ether (25 mL each). The organic extracts were combined, washed with water, and dried over anhydrous magnesium sulfate. The solvent was evaporated leaving an oily product. The oily product was induced to crystallize from diethyl ether. The solid product was suction filtered, washed with hexane and air dried, leaving 2.5 grams of the recovered product. The recovered product had a melting point of 154°–155° C. A nuclear magnetic resonance (NMR) spectrum showed the product to have a structure consistent with 2,2-diphenyl-5-methoxycarbonyl-6-(3-dimethylaminopropyl)methylamino-2H-naphtho[1,2-b]pyran. Upon acidification and illumination with ultraviolet light, an aqueous solution of the product exhibited a red color.

EXAMPLE 3

The 2,2-diphenyl-5-methoxycarbonyl-6-(3-dimethylaminopropyl)methylamino-2H-naphtho[1,2-b]pyran (2 grams) prepared in Example 2, Step 2, was added to a reaction flask containing anhydrous tetrahydrofuran (50 mL) and stirred at room temperature. Lithium aluminum hydride (1 gram) was added slowly to the flask and stirred for two hours. A 5 weight percent hydrochloric acid solution (100 mL) was added and stirred for one half hour. The aqueous layer was separated, washed with diethyl ether (25 mL), and neutralized with a 10 weight percent sodium hydroxide solution. The resulting neutral solution was extracted ten times with diethyl ether (20 mL each). The organic extracts were combined, washed with water, and dried over anhydrous magnesium sulfate. The solvent was evaporated leaving 1 gram of an oily product. A nuclear magnetic resonance (NMR) spectrum showed the product to have a structure consistent with 2,2-diphenyl-5-methylol-6-(3-dimethylaminopropyl)methylamino-2H-naphtho[1,2-b]pyran. Upon acidification and illumination with ultraviolet light, an aqueous solution of the product exhibited a red color.

The present invention has been described with reference to specific details of particular embodiments thereof. It is not intended that such details be regarded as limitations upon the scope of the invention except insofar as to the extent that they are included in the accompanying claims.

What is claimed is:

1. A compound represented by the following graphic formulae:

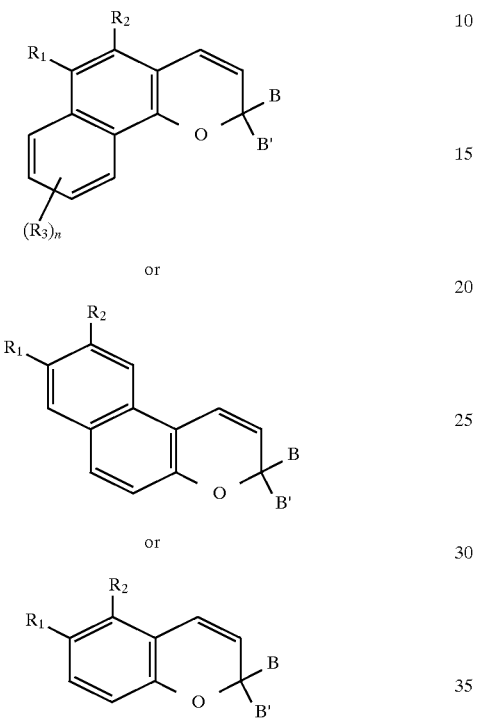

or its free base wherein, (a) $R_1$ is the group represented by the following graphic formula

wherein $R_4$ is $C_1$–$C_3$ alkyl, phenyl($C_1$–$C_3$)alkyl, phenyl or $R_5$, A is an anion selected from the group consisting of chloride, bromide, sulfate and phosphate and $R_5$ is the group represented by the following graphic formula:

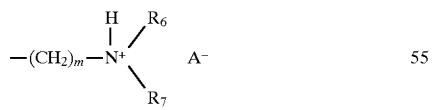

wherein $R_6$ and $R_7$ are each $C_1$–$C_3$ alkyl or $C_1$–$C_3$ alkylamino($C_1$–$C_3$)alkylamino; and m is 2, 3 or 4;

(b) $R_2$ is the group, —C(O)W or —CH$_2$OH, W being —OR$_8$ or —N(R$_9$)R$_{10}$, wherein R$_8$ is selected from the group consisting of hydrogen, allyl, $C_1$–$C_6$ alkyl, phenyl, mono($C_1$–$C_6$)alkyl substituted phenyl, mono ($C_1$–$C_6$) alkoxy-substituted phenyl, phenyl($C_1$–$C_3$) alkyl, mono($C_1$–$C_6$)alkyl substituted phenyl($C_1$–$C_3$) alkyl, mono($C_1$–$C_6$)alkoxy substituted phenyl($C_1$–$C_3$) alkyl, $C_1$–$C_6$ alkoxy($C_2$–$C_4$)alkyl, and $C_1$–$C_6$ haloalkyl, and wherein R$_9$ and R$_{10}$ are each selected from the group consisting of hydrogen, $C_1$–$C_6$ alkyl, $C_5$–$C_7$ cycloalkyl, phenyl and mono- or di-substituted phenyl, said phenyl substituents being $C_1$–$C_6$ alkyl or $C_1$–$C_6$ alkoxy and said halo substituents being chloro or fluoro;

(c) each $R_3$ is $C_1$–$C_6$ alkyl, $C_3$–$C_7$ cycloalkyl, substituted or unsubstituted phenyl or the group —OR$_{11}$, wherein R$_{11}$ is hydrogen or ($C_1$–$C_6$)alkyl, said phenyl substituents being selected from $C_1$–$C_6$ alkyl o,r $C_1$–$C_6$ alkoxy, and n is 0, 1 or 2; and (d) B and B' are each selected from the group consisting of:

(i) the unsubstituted, mono-, di- and tri-substituted aryl groups, phenyl and naphthyl;

(ii) the unsubstituted, mono- and di-substituted heteroaromatic groups pyridyl, furanyl, benzofuran-2-yl, benzofuran-3-yl, thienyl, benzothien-2-yl, benzothien-3-yl, dibenzofuranyl, dibenzothienyl, carbazolyl and fluorenyl, each of said aryl and heteroaromatic substituents in (d) (i) and (ii) being selected from the group consisting of hydroxy, aryl, mono($C_1$–$C_6$)alkoxyaryl, di($C_1$–$C_6$)alkoxyaryl, mono($C_1$–$C_6$)alkylaryl, di($C_1$–$C_6$)alkylaryl, bromoaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy($C_1$–$C_6$)alkoxy, aryl($C_1$–$C_6$) alkyl, aryl($C_1$–$C_6$)alkoxy, aryloxy, aryloxy($C_1$–$C_6$) alkyl, aryloxy($C_1$–$C_6$)alkoxy, mono- and di($C_1$–$C_6$) alkylaryl($C_1$–$C_6$)alkyl, mono- and di($C_1$–$C_6$) alkoxyaryl($C_1$–$C_6$)alkyl, mono- and di($C_1$–$C_6$) alkylaryl($C_1$–$C_6$)alkoxy, mono- and di($C_1$–$C_6$) alkoxyaryl($C_1$–$C_6$)alkoxy, amino, mono($C_1$–$C_6$) alkylamino, di($C_1$–$C_6$)alkylamino, diarylamino, N($C_1$–$C_6$)alkylpiperazino, N-arylpiperazino, aziridino, indolino, piperidino, arylpiperidino, morpholino, thiomorpholino, tetrahydroquinolino, tetrahydroisoquinolino, pyrryl, $C_1$–$C_6$ alkyl, $C_1$–$C_6$ bromoalkyl, $C_1$–$C_6$ chloroalkyl, $C_1$–$C_6$ fluoroalkyl, $C_1$–$C_6$ alkoxy, mono($C_1$–$C_6$)alkoxy($C_1$–$C_4$)alkyl, acryloxy, methacryloxy, bromo, chloro and fluoro;

(iii) the groups represented by the following graphic formulae:

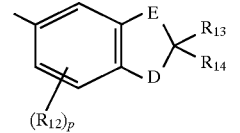

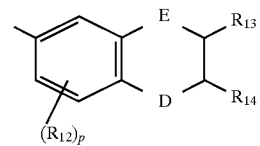

wherein E is carbon or oxygen and D is oxygen or substituted nitrogen, provided that when D is substituted nitrogen, E is carbon, said nitrogen substituents being selected from the group consisting of hydrogen, $C_1$–$C_6$ alkyl and $C_2$–$C_6$ acyl; each R$_{12}$ is $C_1$–$C_6$ alkyl, $C_1$–$C_6$ alkoxy, hydroxy, bromo, chloro or fluoro; R$_{13}$ and R$_{14}$ are each hydrogen or $C_1$–$C_6$ alkyl; and p is 0, 1 or 2;

(iv) $C_1$–$C_6$ alkyl, $C_1$–$C_6$ bromoalkyl, $C_1$–$C_6$ chloroalkyl, $C_1$–$C_6$ fluoroalkyl, $C_1$–$C_6$ alkoxy ($C_1$–$C_4$)alkyl, $C_3$–$C_6$ cycloalkyl, mono($C_1$–$C_6$) alkoxy($C_3$–$C_6$)cycloalkyl, mono($C_1$–$C_6$)alkyl ($C_3$–$C_6$)cycloalkyl, bromo($C_3$–$C_6$)cycloalkyl, chloro ($C_3$–$C_6$)cycloalkyl and fluoro($C_3$–$C_6$)cycloalkyl; and (v) the group represented by the following graphic formula:

wherein X is hydrogen or $C_1$–$C_4$ alkyl and Y is selected from the unsubstituted, mono-, and di-substituted members of the group consisting of naphthyl, phenyl, furanyl and thienyl, each of said group substituents in this part (v) being $C_1$–$C_4$ alkyl, $C_1$–$C_4$ alkoxy, bromo, fluoro or chloro; or (vi) B and B' taken together form fluoren-9-ylidene, mono- or di-substituted fluoren-9-ylidene or a member selected from the group consisting of saturated $C_3$–$C_{12}$spiro-monocyclic hydrocarbon rings, saturated $C_7$–$C_{12}$ spiro-bicyclic hydrocarbon rings, and saturated $C_7$–$C_{12}$ spiro-tricyclic hydrocarbon rings, each of said fluoren-9-ylidene substituents being selected from the group consisting of $C_1$–$C_4$ alkyl, $C_1$–$C_4$ alkoxy, bromo, fluoro and chloro.

2. The compound of claim 1 wherein:

(a) $R_1$ is the group represented by the following graphic formula:

wherein $R_4$ is methyl or 3-dimethylaminopropyl and $R_5$ is the group represented by the following graphic formula:

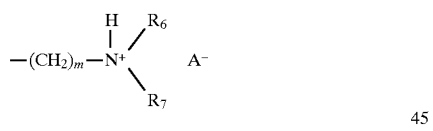

wherein m is 2, 3 or 4;

(b) $R_2$ is the group —C(O)W, W being the groups —$OR_8$ or —N($R_9$)$R_{10}$, wherein $R_8$ is selected from the group consisting of hydrogen, $C_1$–$C_4$ alkyl, phenyl, mono ($C_1$–$C_4$)alkyl substituted phenyl, mono($C_1$–$C_4$)alkoxy substituted phenyl, phenyl($C_1$–$C_2$)alkyl, mono($C_1$–$C_4$) alkyl substituted phenyl($C_1$–$C_2$)alkyl, mono($C_1$–$C_4$) alkoxy substituted phenyl($C_1$–$C_2$)alkyl, mono($C_1$–$C_4$) alkoxy($C_2$–$C_3$)alkyl, and $C_1$–$C_4$ haloalkyl and wherein $R_9$ and $R_{10}$ are each selected from the group consisting of hydrogen, $C_1$–$C_4$ alkyl, $C_5$–$C_7$ cycloalkyl, phenyl and mono- or di-substituted phenyl, said phenyl substituents being $C_1$–$C_4$ alkyl or $C_1$–$C_4$ alkoxy, said halo substituents being chloro or fluoro;

(c) each $R_3$ is hydrogen, $C_1$–$C_3$ alkyl, $C_3$–$C_5$ cycloalkyl substituted or unsubstituted phenyl or —$OR_{11}$, wherein $R_{11}$ is hydrogen or $C_1$–$C_3$ alkyl, said phenyl substituents being $C_1$–$C_3$ alkyl or $C_1$–$C_3$ alkoxy and n is 0 or 1; and (d) B and B' are each selected from the group consisting of:

(i) phenyl, mono-substituted phenyl and di-substituted phenyl;

(ii) the unsubstituted, mono-substituted and di-substituted heteroaromatic groups furanyl, benzofuran-2-yl, thienyl, benzothien-2-yl, dibenzofuran-2-yl, and dibenzothien-2-yl, each of -said phenyl and heteroaromatic substituents in (d)(i) and (ii) being selected from the group consisting of hydroxy, aryl, aryloxy, aryl($C_1$–$C_3$)alkyl, amino, mono($C_1$–$C_3$)alkylamino, di($C_1$–$C_3$)alkylamino, N($C_1$–$C_3$)alkylpiperazino, indolino, piperidino, morpholino, pyrryl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$) alkoxy($C_1$–$C_3$)alkyl, fluoro and chloro;

(iii) the groups represented by the following graphic formulae:

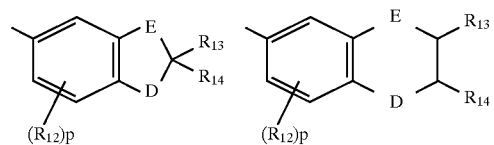

wherein E is carbon and D is oxygen, $R_{12}$ is $C_1$–$C_3$ alkyl or $C_1$–$C_3$ alkoxy, $R_{13}$ and $R_{14}$ are each hydrogen or $C_1$–$C_4$ alkyl; and p is 0 or 1;

(iv) $C_1$–$C_4$ alkyl; and (v) the group represented by the following graphic formula:

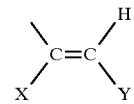

wherein X is hydrogen or methyl and Y is phenyl or mono-substituted phenyl, said phenyl substituent being selected from the group consisting of $C_1$–$C_3$ alkyl, $C_1$–$C_3$ alkoxy and fluoro; or (vi) B and B' taken together form a fluoren-9 -ylidene, mono-substituted fluoren-9-ylidene or a member selected from the group consisting of saturated $C_3$–$C_8$ spiro-monocyclic hydrocarbon rings, saturated $C_7$–$C_{10}$ spiro-bicyclic hydrocarbon rings and saturated $C_7$–$C_{10}$ spiro-tricyclic hydrocarbon rings, said fluoren-9-xylidene substituent being selected from the group consisting of $C_1$–$C_3$ alkyl, $C_1$–$C_3$ alkoxy, fluoro and chloro.

3. The compound of claim 2 wherein (a) $R_1$ is the group represented by the following graphic formula:

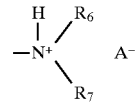

wherein $R_4$ is methyl or 3-dimethylaminopropyl and $R_5$ is 3-dimethylaminopropyl;

(b) $R_2$ is the group —C(O)W, W being the group —$OR_8$ wherein $R_8$ is $C_1$–$C_3$ alkyl; and (c) B and B' are each selected from the group consisting of:

(i) phenyl, mono-substituted and di-substituted phenyl;

(ii) the unsubstituted, mono-, and di-substituted heteroaromatic groups furanyl, benzofuran-2-yl, thienyl and benzothien-2-yl, each of said phenyl and heteroaromatic substituents in (c)(i) and (ii) being selected from the group consisting of hydroxy, $C_1$–$C_3$ alkyl, $C_1$–$C_3$ alkoxy, aryl, indolino, fluoro and chloro; and (iii) the group represented by the following graphic formula:

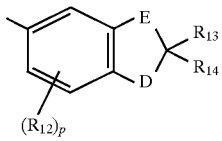

wherein E is carbon and D is oxygen, $R_{12}$ is $C_1$–$C_3$ alkyl or $C_1$–$C_3$ alkoxy, $R_{13}$ and $R_{14}$ are each hydrogen or $C_1$–$C_3$ alkyl, and p is 0 or 1; or (iv) B and B' taken together form fluoren-9-ylidene, adamantylidene, bornylidene, norbornylidene or bicyclo(3.3.1)nonan-9-ylidene.

4. A photochromic article comprising a polymeric organic host material selected from the group consisting of poly (methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol bismethacrylate monomers, diisopropenyl benzene monomers and ethoxylated trimethylol propane triacrylate monomers and a photochromic amount of the compound of claim 3.

5. A photochromic composition comprising a coating composition and a photochromic amount of the compound of claim 3.

6. The photochromic composition of claim 5 wherein said compound is water soluble.

7. The photochromic composition of claim 6 wherein the water solubility of said compound is at least one gram per liter.

8. A photochromic article comprising a polymeric organic host material and a photochromic amount of the compound of claim 1.

9. The photochromic article of claim 8 wherein the polymeric organic host material is selected from the group consisting of poly($C_1$–$C_{12}$ alkyl methacrylates), poly(oxyalkylene dimethacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of bis(allyl carbonate) monomers, polyfunctional acrylate monomers, polyfunctional methacrylate monomers, diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers, alkoxylated polyhydric alcohol acrylate monomers, styrene monomers, urethane acrylate monomers, glycidyl acrylate monomers, glycidyl methacrylate monomers and diallylidene pentaerythritol monomers.

10. The photochromic article of claim 9 wherein the polymeric organic host material is a solid transparent polymer selected from the group consisting of poly(methyl methacrylate), poly(ethylene glycol bismethacrylate), poly (ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers.

11. The photochromic article of claim 10 wherein the photochromic compound is present in an amount of from 0.05 to 1.0 milligram per square centimeter of organic host material surface to which the photochromic substance(s) is incorporated or applied.

12. The photochromic article of claim 11 wherein said transparent polymer is an optical element.

13. The photochromic article of claim 12 wherein said optical element is a lens.

14. A photochromic composition comprising a coating composition and a photochromic amount of the compound of claim 1.

15. The photochromic composition of claim 14 wherein said compound is water soluble.

16. The photochromic composition of claim 15 wherein the water solubility of said compound is at least about one gram per liter.

17. The photochromic composition of claim 14 wherein the coating composition is chemically compatible with said compound and is substantially free of ultraviolet light absorbing materials in amounts that interfere with the activation of said compound.

18. A compound selected from the group consisting of:

(a) 2,2-bis(4-methoxyphenyl)-5-methoxycarbonyl-6-bis(3-dimethylaminopropyl)amino-2H-naphtho [1,2-b]pyran;

(b) 2,2-diphenyl-5-methoxycarbonyl-6-(3-dimethylaminopropyl)methylamino-2H-naphtho[1,2-b]pyran;

(c) 2,2-diphenyl-5-methylol-6-(3-dimethylaminopropyl)methylamino-2H-naphtho[1,2-b]pyran;

(d) 3,3-bis(4-methoxy phenol)-8-bis(3-dimethylaminopropyl)amino-3H-naphtho[2,1-b]pyran;

(e) 3,3-diphenyl-8-(3-dimethylaminopropyl)-methylamino-3H-naphtho[2,1-b]pyran; and (f) 2,2-diphenyl-5-methoxycarbonyl-6-bis(3-dimethylaminopropyl)amino-2H-benzopyran.

19. A compound comprising a quaternary ammonium salt of the compound of claim 18.

20. A photochromic article comprising a polymeric oganic host material selected from the group consisting of poly (methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol bismethacrylate monomers, diisopropenyl benzene monomers and ethoxylated trimethylol propane triacrylate monomers, and a photochromic amount of the compound of claim 19.

* * * * *